US008764650B2

(12) United States Patent
Schiavenato et al.

(10) Patent No.: US 8,764,650 B2
(45) Date of Patent: Jul. 1, 2014

(54) METHODS AND SYSTEMS FOR MEASURING AND COMMUNICATING PAIN AND DISTRESS LEVEL

(75) Inventors: Martin Schiavenato, Rochester, NY (US); Laurel H. Carney, Geneva, NY (US); Scott Seidman, Fairport, NY (US)

(73) Assignee: University of Rochester, Rochester, NY (US)

(*) Notice: Subject to any disclaimer, the term of this patent is extended or adjusted under 35 U.S.C. 154(b) by 119 days.

(21) Appl. No.: 13/267,842

(22) Filed: Oct. 6, 2011

(65) Prior Publication Data

US 2012/0088985 A1 Apr. 12, 2012

Related U.S. Application Data

(60) Provisional application No. 61/390,482, filed on Oct. 6, 2010, provisional application No. 61/409,037, filed on Nov. 1, 2010.

(51) Int. Cl.
*A61B 5/00* (2006.01)
*G06F 19/00* (2011.01)

(52) U.S. Cl.
CPC .............. *G06F 19/30* (2013.01); *A61B 5/4824* (2013.01); *G06F 19/322* (2013.01); *G06F 19/3431* (2013.01)
USPC .......................................... 600/300; 600/301

(58) Field of Classification Search
None
See application file for complete search history.

(56) References Cited

U.S. PATENT DOCUMENTS

| 4,844,091 | A | * | 7/1989 | Bellak | 600/557 |
| 5,897,505 | A | * | 4/1999 | Feinberg et al. | 600/547 |
| 6,146,334 | A | * | 11/2000 | Laserow | 600/552 |
| 6,571,124 | B1 | * | 5/2003 | Storm | 600/547 |
| 6,654,632 | B2 | * | 11/2003 | Lange et al. | 600/544 |
| 7,097,617 | B1 | * | 8/2006 | Smith | 600/300 |
| 7,407,485 | B2 | * | 8/2008 | Huiku | 600/300 |
| 7,991,462 | B2 | * | 8/2011 | Storm | 600/547 |
| 2002/0138018 | A1 | * | 9/2002 | Lange et al. | 600/544 |
| 2005/0272984 | A1 | * | 12/2005 | Huiku | 600/301 |
| 2006/0217615 | A1 | * | 9/2006 | Huiku et al. | 600/484 |
| 2006/0217628 | A1 | * | 9/2006 | Huiku | 600/544 |
| 2008/0249430 | A1 | * | 10/2008 | John et al. | 600/544 |
| 2010/0132058 | A1 | * | 5/2010 | Diatchenko et al. | 800/9 |

OTHER PUBLICATIONS

Kliger et al. WO 2010/134068 A1 (attached PDF).*
Borg, G., Holmgren, A., & Limblad, I. (1981). "Quantitative evaluation of chest pain", Acta Medica Scandinavica, Supplementum, 644, 43-45.

(Continued)

*Primary Examiner* — Bill Thomson
*Assistant Examiner* — Shirley Jian
(74) *Attorney, Agent, or Firm* — James W. Hill; McDermott Will & Emery LLP

(57) ABSTRACT

Systems and methods are described for communicating the distress or pain experienced by an infant or a non-communicative patient. The systems and methods can provide an objective quantification of pain and/or distress in conjunction with, e.g., various distressing procedures commonly found in the newborn intensive care unit (NICU). The systems may include a processor in communication with a distress level input device and a display configured to provide a representation of a pain or distress score calculated in the processor. The processor may include executable code to translate data from the distress level input into the distress score.

21 Claims, 7 Drawing Sheets

(56) References Cited

OTHER PUBLICATIONS

Cardello, A., Schultz, H.G., Lesher, L.L., & Merrill, E. (2005). "Development and testing of a labeled magnitude scale perceived satiety", Appetite, 44(1), 1-13.

Hoisti., L., Grunau, R.E. (2007). "Initial validation of the behavioral indicators of infant pain (BIIP)" Pain 132(3), 264.

Kee. D., & Karwowski, W. (2003). "Ranking systems for evaluation of joint and joint motion stressfulness based on perceived discomforts", Applied Ergonomics, 34(2), 167-176.

Meek, P.M., Sennott-Miller, L., & Ferketich. S.L. (1992). "Focus on psychometrics, scaling stimuli with magnitude estimation", Research in Nursing & Health, 15(1), 77-81.

* cited by examiner

Flexure Sensor Circuit

METHODS AND SYSTEMS FOR MEASURING AND COMMUNICATING PAIN AND DISTRESS LEVEL

RELATED APPLICATIONS

This application claims priority benefit of U.S. Provisional Application No. 61/390,482, filed on Oct. 6, 2010, and U.S. Provisional Application No. 61/409,037, filed on Nov. 1, 2010; the entirety of each of which is incorporated herein by reference.

BACKGROUND

Infants in the newborn intensive care unit (NICU) are vulnerable due in part to the critical stage of their neurodevelopment and also because of the noxious nature of many procedures that they experience as part of the standard and common life-saving interventions that they bear. Such procedures can range from something as innocuous as a diaper change to invasive "skin breaking" procedures, such as catheter placements and circumcision.

Each of these procedures can be cause for pain and distress in infants and possibly associated with both immediate and longer-term poor health outcomes. Simply put, procedures undertaken by these infants can carry a neurological burden or load that may be harmful to infant development. Currently, there is controversy in the literature as to when and how procedures should be performed in the NICU; with some advocating for the grouping or "clustering" of procedures, and others pointing to the detrimental synergistic effects of such a strategy. Because an average of 14 distress-causing procedures are performed on these infants in the NICU per day, it can be advantageous for clinicians to better understand the effects of these procedures.

The measurement, monitoring, and/or indication of distress and pain may assist clinicians in determining, in a clinically meaningful manner, the timing, number, and nature of procedures to be performed. Distress and pain, however, are a challenge to measure, and particularly so with non-communicative or non-verbal patients, such as newborn infants. Some methodologies for measuring pain in newborns includes the use of "pen and paper" scales that are filled out by clinicians to arrive at what is commonly referred to as a "pain score."

SUMMARY

Because determinations of measuring pain can be rather subjective, clinicians also monitor vitals signs, such as heart rate and respiration, determine pain and distress experienced by an infant. Notwithstanding the use of these pain measuring methodologies, however, presently there is no metric to quantify the distress and pain associated with the procedures themselves. Consequently, there is no formal way of measuring the potential impact of a clinicians' actions, or of quantitatively anticipating the potential effect of routine procedural interventions. Existing attempts at quantifying and classifying procedural distress intensity are limited to investigational methods (i.e., not clinical or bedside tools) and are at best categorical. Having a more precise means of estimating procedure-associated distress in patients, such as infants may help clinicians make better-informed decisions about the potential effects of the procedure and the subsequent timing or delivery of additional procedures.

It can be advantageous, therefore, to have systems and methods for effectively communicating the distress or pain experienced by the patients. It can also be advantageous to have an objective quantification of procedural distress in the NICU and/or a tool to track and display the current state of distress of patients, such as newborn infants, based on the nature of the clinical procedures experienced.

The subject technology generally relates to patient care and pain management and, in particular, to methods and systems for detecting, monitoring, and indicating pain and/or distress and various methods and systems for communicating a pain level for a patient.

According to various embodiments of the subject technology, methods of communicating a pain level of a patient are disclosed. The methods may include acquiring objective measurements of one or more parameters associated with the pain level, and translating the one or more parameters into a single pain score. In some embodiments two or more parameters are translated into a single pain score. The methods may further include displaying a representation of the single pain score. In some embodiments, acquiring the objective measurements of one or more parameters associated with the pain level may include one or more of acquiring a signal corresponding to heart rate of the patient, acquiring a signal corresponding to facial electromyography of the patient, and/or acquiring a signal corresponding to hand flexing of the patient. In one embodiment, the acquired signal may be a heart rate variability signal. In some embodiments, translating the one or more parameters into a single pain score includes adding the one or more parameters, applying Boolean logic to the one or more parameters, and/or processing the one or more parameters with a neural network. In some embodiments, the representation of the single pain score comprises a visual representation, such as visible light. In at least one embodiment, the visible light is emitted from a ball or orb, such as a frosted-glass ball According to various embodiments of the subject technology, systems are provided for measuring and communicating pain level. The system may include a sensory level input device, and a processor communicably coupled to the sensory level input device, the processor having executable code configured to translate data received from the sensory level input device into a pain score. The system may further include a display configured to provide a representation of the pain score. In some embodiments, the sensory level input device is configured to provide data about one or more pain level parameters. The sensory level input device may include one or more of an electrocardiogram monitor configured to provide data about heart rate, a facial electromyography monitor configured to provide data about facial electromyography, and/or a hand flexure sensor to provide data about hand flexing. In some embodiments, the sensory level input device may include an interface configured for use by a clinician, and the processor may utilize a procedure load index to translate the data received from the sensory level input device into the pain score.

In some embodiments, the representation of the pain score includes an indication of decay of the pain score over time. In other embodiments, the display provides a visual representation of the pain score, wherein the display comprises a ball or orb, and the visual representation comprises a colored light emitted from the ball or orb. In some embodiments, the processor may be configured to translate the data received from the one or more pain level parameters by summing the data, applying Boolean logic to the data, and/or processing the data with a neural network. In other embodiments, the processor and the display are housed in a tablet PC.

According to various embodiments of the subject technology, methods of measuring distress in a patient are disclosed.

The methods may include acquiring an objective indication of a distress level of the patient, and translating data from the indication of the distress level into a distress score. The methods may further include displaying a representation of the distress score on a display. In some embodiments, acquiring the objective indication of the distress level of the patient may include assigning the distress level based on selection of a particular distressing procedure, and translating data from the indication of the distress level into the distress score can include looking up a pre-determined distress level associated with the particular distressing procedure in a procedure load index. In some embodiments, the methods may further include calculating future distress scores, and displaying the calculated future distress scores, where calculating future distress scores comprises applying a distress score decay rate to the distress score.

According to various embodiments of the subject technology, methods of determining when to perform a distressing procedure are disclosed. The methods may include determining a first distress score and determining a second distress score. The methods may also include determining whether the combination of the first distress score and the second distress score exceed a predetermined limit. In some embodiments, determining the first distress score further includes acquiring objective indication of a first distress level, and translating data from the indication of the first distress level into the first distress score. In at least one embodiment, acquiring objective indication of distress level can include clinician input of the distress level. In some embodiments, the first distress score includes distress measured from at least one prior distressing procedure. The first distress score may have decayed at a predetermined rate from an initial distress score present at the time of the prior distressing procedure. In some embodiments, the second distress score is determined by looking up the distressing procedure in a procedure load index. In one or more embodiments, the methods may further include projecting decay of the first distress score and the second distress score and calculating when the combination of the first distress score and the second distress score will fall below the predetermined limit. In other embodiments, the methods may further include calculating a third distress score and determining whether the combination of the first distress score, the second distress score, and the third distress score exceed the predetermined limit.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

Figure 1:
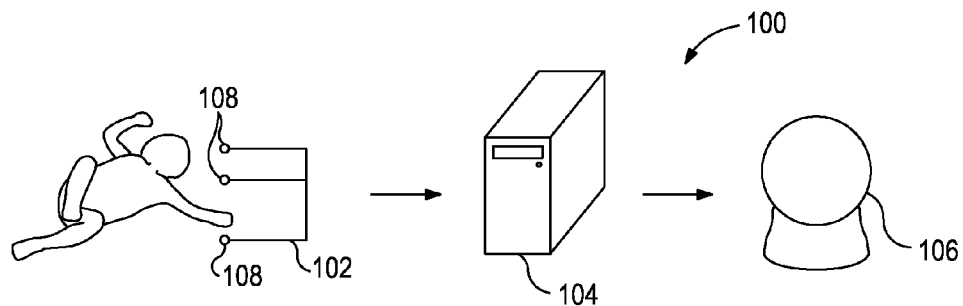
FIG. 1 illustrates an exemplary system for communicating pain level, in accordance with various embodiments of the subject technology.

FIG. 1 illustrates is a system 100 for communicating a pain or distress level experienced by a patient, according to one or more aspects of the disclosure. The system 100 includes a sensory level input device 102, a processor 104, and a display 106. The system 100 may be a standalone bedside device having separate components, or it may be incorporated into a larger system, such as a bedside monitor or an infusion pump.

The sensory level input device 102 may include one or more sensory inputs 108 configured to measure and collect data about one or more pain level parameters. While only three sensory inputs 108 are depicted in FIG. 1, more or less than three sensory inputs 108 may be employed without departing from the scope of the disclosure. The processor 104 is communicably coupled, either wired or wirelessly, to the sensory level input device 102 and includes executable code configured to translate the data received from the sensory level input device 102 into a pain score, also characterized herein as a distress score. The display 106 is communicably coupled, either wired or wirelessly, to the processor 104 and configured to provide a representation of pain score.

In exemplary operation, the system 100 measures, monitors, and indicates distress and/or pain associated with distress-causing procedures experienced by vulnerable patients, such as infants in the newborn intensive care unit (NICU) and/or other non-communicative individuals. Such distress-causing procedures can range from invasive procedures, such as catheter placements, to seemingly innocuous procedures, such as diaper changes. The system 100 combines various behavioral and physiologic signs implicated in pain experience and expression into one objective, real-time output provided at the bedside of the vulnerable patient. This real-time output is provided via the display 106 and can be in the form of a digitally-displayed number, a visual indicator, an auditory indicator, or any other output designed to alert the clinician of a calculated pain or distress score registered by the patient.

In some embodiments, the display 106 may be an ambient device, such as a frosted-glass ball or orb (as illustrated), that is capable of changing color or light intensity in response to the input received from the processor 104. In other embodiments, the display 106 may be an LED or other light-emitting interface adapted to represent the output provided from the processor 104 in a subtle, intuitive, and clear manner. Accordingly, changes in the status of the patient, such as an increase in pain, may be easily recognizable as a change in color or intensity of light emitted by the display 106. This approach may prove beneficial since it provides a clinician with immediate feedback from the vulnerable patient as to her status related to clinically-relevant signs of pain.

In some embodiments, the display 106 may be a computer monitor or screen, or any other device or apparatus capable of providing a visual or otherwise quantifiable representation of the pain score to the clinician. In some embodiments, the display 106 may include speakers or other types of auditory devices capable of providing the clinician with an audible alert as to pain or distress experienced by the patient.

Figure 2:
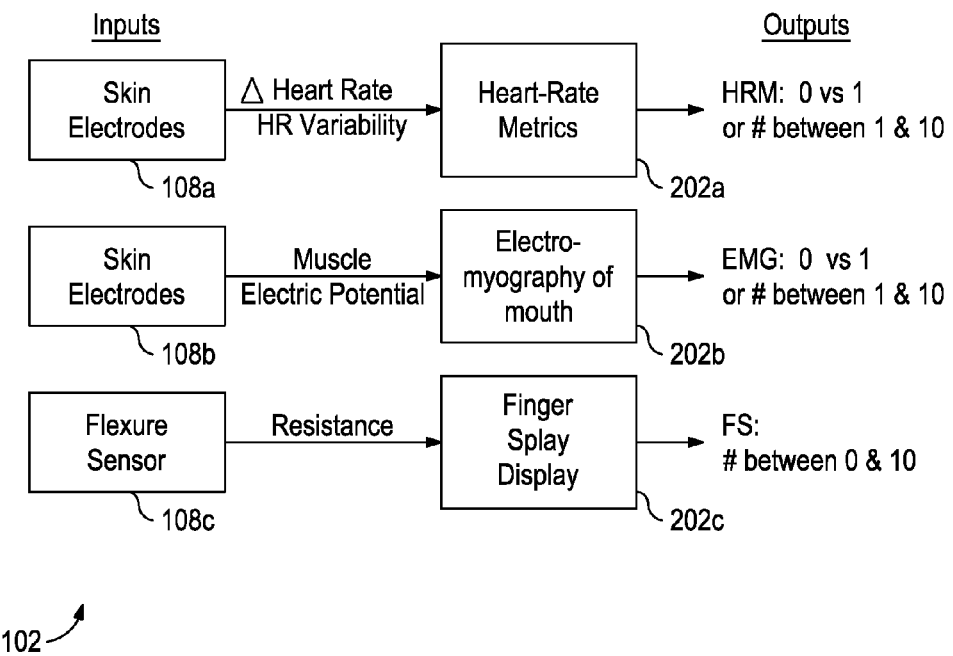
FIG. 2 illustrates examples of various sensory level input devices, in accordance with various embodiments of the subject technology.

Referring now to FIG. 2, the one or more sensory inputs 108 (shown as first, second, and third sensory inputs 108a, 108b, and 108c, respectively) in the sensory level input device 102 may be configured to acquire various signals associated with pain level parameters that reflect distress and/or pain in the patient. The rationale behind the selection of the signals derived by the first, second, and third sensory inputs 108a-c is founded on their involvement in the pain display 106. Acquiring distress and/or pain signals involves the gathering of specific behavioral and/or physiologic displays of pain, whether induced internally or externally on the patient.

As illustrated, the sensory level input device 102 may monitor and acquire several types of signals associated with corresponding pain level parameters, such as heart rate metrics 202a (e.g., heart rate and heart rate variability (HRV)), electromyography of the mouth (EMG) 202b (e.g., facial grimacing), and/or finger splaying (FS) 202c. As can be appreciated, several other types of distress and pain signals corresponding to other pain level parameters may be acquired via the sensory level input device 102 such as, but not limited to, galvanic skin response (GSR) signals, electroencephalography (EEG) signals, near-infrared spectroscopy (NIRS) signals, combinations thereof, or the like. The ultimate decision as to how many and which combination of signals is ideal or required may vary depending on the application.

Figure 3:
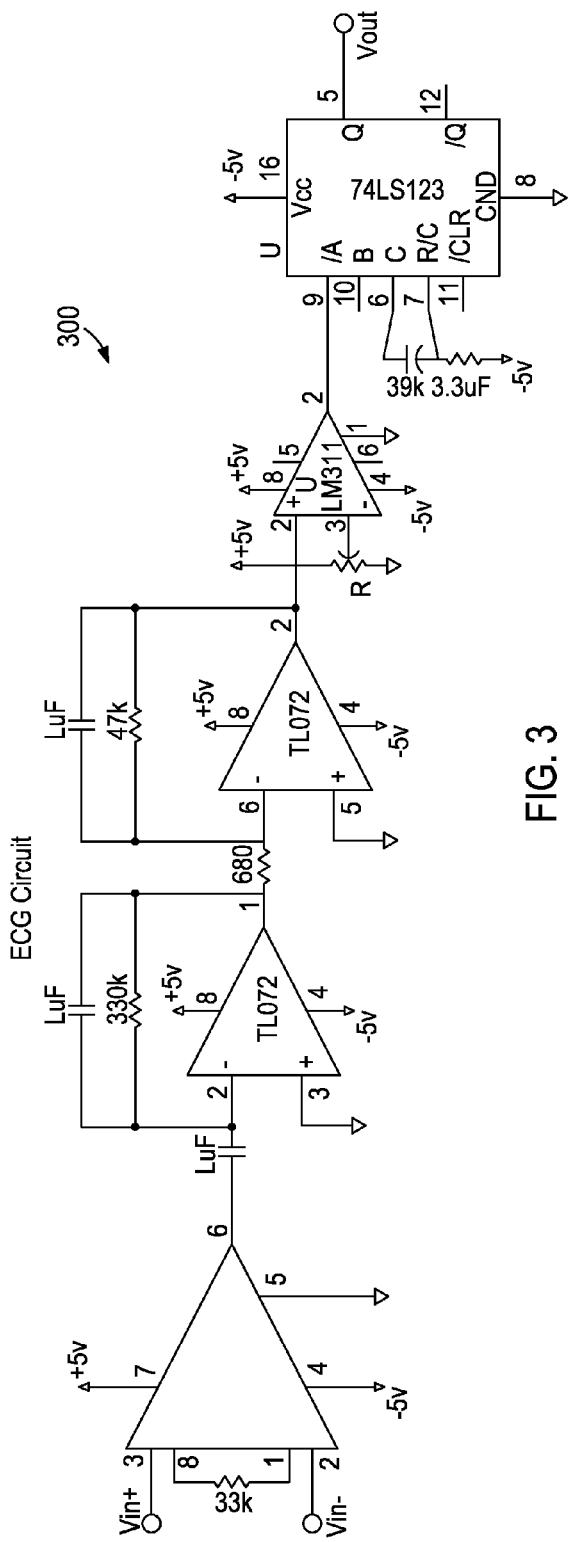
FIGS. 3-5 illustrate examples of circuit diagrams that produce a pain level parameter signal for sensory level input devices, in accordance with various embodiments of the subject technology.

As shown in FIG. 2, the first sensory input 108a may be configured to capture heart rate and/or HRV corresponding to the first pain level parameter 202a. The first sensory input 108a may include an electrocardiogram signal commonly outputted by existing technology, such as a GENERAL ELECTRIC® NICU monitor or other electrocardiogram monitors that provide data about heart rate, or may be any external device adapted to provide heartbeat or pulse detection. The signal may be derived through an electrocardiogram circuit, such as the exemplary circuit 300 illustrated in FIG. 3. It will be appreciated, however, that various forms of the electrocardiogram circuit 300 may be employed to obtain the desired signal, without departing from the scope of the disclosure. The signal may be acquired via one or more skin electrodes, processed by the sensory level input device 102, or otherwise, through an algorithm, changed from time domain to a frequency domain, and a specific frequency in the HRV may be monitored for indications of pain/distress.

Figure 4:
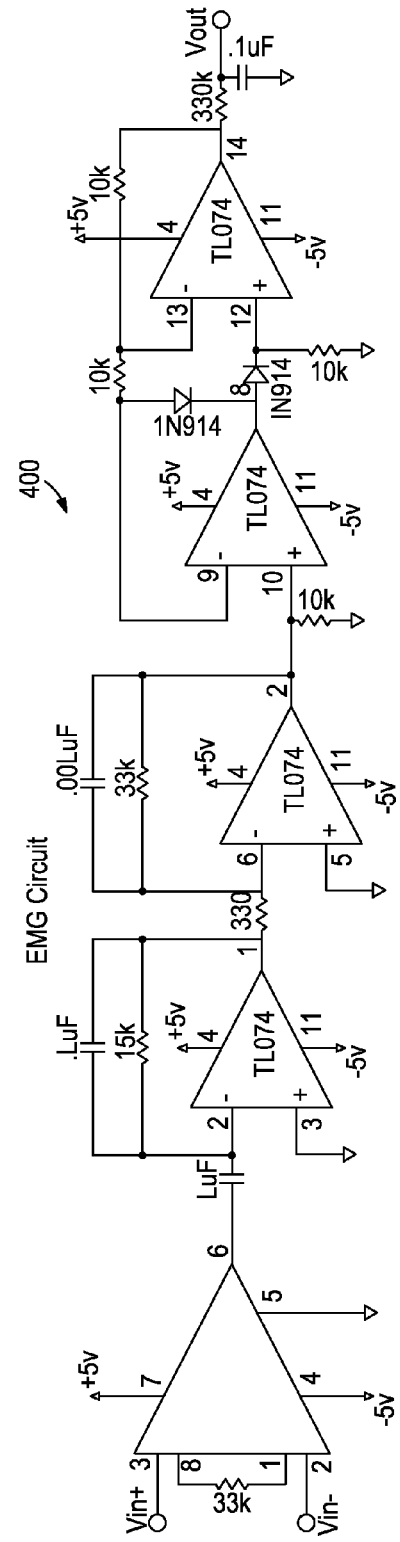

Still referring to FIG. 2, the second sensory input 108b may be configured to capture facial grimacing of the patient corresponding to the second pain level parameter 202b. The second sensory input 108b may include a facial electromyography monitor adapted to provide data about facial electromyography. In some embodiments, facial grimacing may be captured by one or more skin electrodes placed over a specific area of the face that indicate a vertical opening of the mouth, thereby providing an associated electromyography (EMG) signal. The EMG signal may be processed through several types of EMG circuits, such as, but not limited to, the EMG circuit illustrated in FIG. 4.

Figure 5:
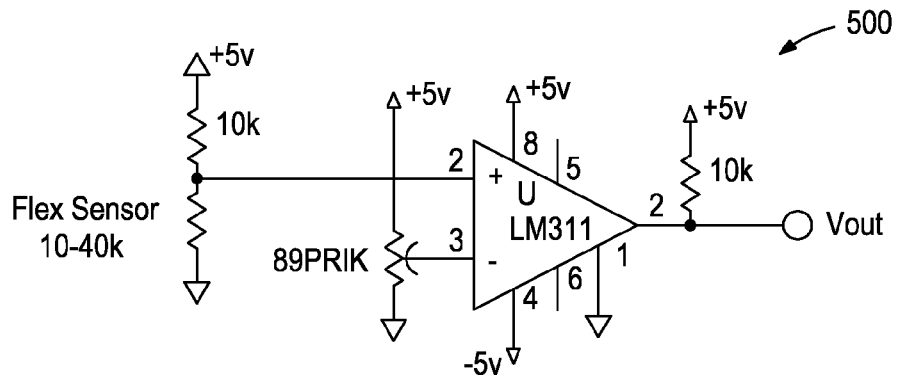

Finger splaying (FS) may be captured by the third sensory input 108c corresponding to the third pain level parameter 202c. To obtain appropriate FS signals, a small hand flexure sensor may be used, the flexure sensor being configured to provide data about hand flexing on the palm of the hand of the patient. In operation, the flexure sensor senses the opening and closing of the hand and, via standard bedside electrodes, provides the FS signal. The design of the flexure sensor may combine various materials and techniques safe enough for the sensitive skin of an infant, yet resilient enough configured to withstand clinical and engineering demands, such as fluctuating temperature and humidity. In some embodiments, the FS signal is obtained through the flexure sensor circuit 500 illustrated in FIG. 5. It will be appreciated, however, that various forms of the flexure sensor circuit 500 may be used to obtain the desired signal, without departing from the scope of the disclosure.

In one or more embodiments, the various signals (e.g., HRV, EMG, and FS) may be interpreted "off line" so as to develop accurate and precise interpretive algorithms of the data. Thus, the signals may be processed and stored on a hard drive for further analysis. For example, the signals may be first collected or otherwise retrieved via the sensory inputs 108a-c, then initially/basically processed in real-time at the bedside of the patient (e.g., yes/no; on/off) using the sensory level input device 102. The resulting signal data is subsequently stored for further algorithm development, such as for research and development purposes. Once the algorithm refinement is satisfactory, the data may be displayed as a signal output for clinical purposes. Displaying the data via the display 106 may be in addition to, or as an alternative to, the storage of the signal data.

Figure 6:
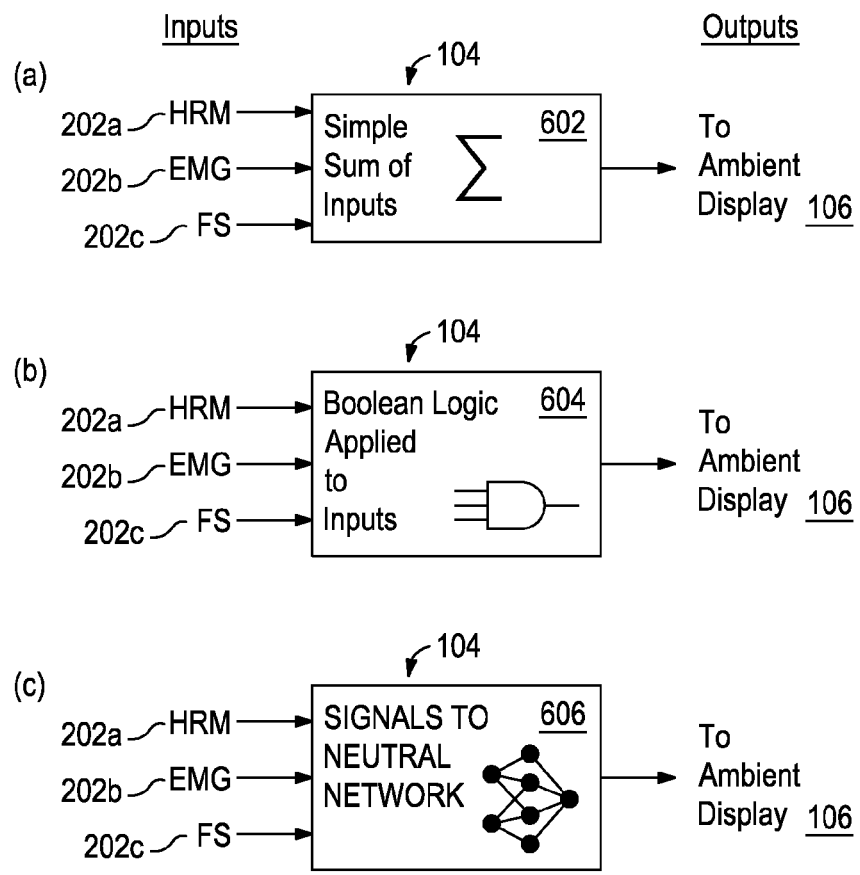
FIG. 6 illustrates an example of signal combination schemes, in accordance with various embodiments of the subject technology.

Once the sensory level input device 102 has collected the data regarding the pain level parameters 202a-c, the data is transmitted to the processor 104 for signal processing. Signal processing may include software and decision making algorithms involved in interpreting signal input data and translating it into a clinically-meaningful metric implemented using microcontroller or other computational techniques. As can be appreciated, various alternatives or techniques for signal processing may be used. For example, as illustrated in FIG. 6, the processor 104 may perform a simple sum of inputs 602, apply Boolean logic to the inputs 604, or use a neural network 606 to provide an output. However, signal processing is not limited to these examples. The output from the processor 104 may be used by or otherwise transmitted to the display 106.

Several advantages are gained using the system 100, as will be apparent to those skilled in the art. For example, an immediate interpretation and visual depiction of pertinent pain and/or distress data is provided to the clinician. Consequently, there is no need to fill out time-intensive paper scales, or calculate individual potential deviations in biophysiologic signs. Also, the system 100 provides an objective, machine-processed, constant display of these data such that subjective human judgment in the form of infant observation for signs is entirely removed. Moreover, the pain score is empirically derived from multiple behavioral and physiological sources (i.e., the pain level parameters). As can be appreciated, multidimensional and triangulated signals may be preferable over individual signals. At least one more advantage of the system 100 may be in the subtle graphic nature of the ambient display 106 (e.g., the ambient orb or ball described above), which is non-intrusive and therefore does not add a potential noxious burden of additional alarms in already loud patient settings, such as the NICU.

Figure 7:
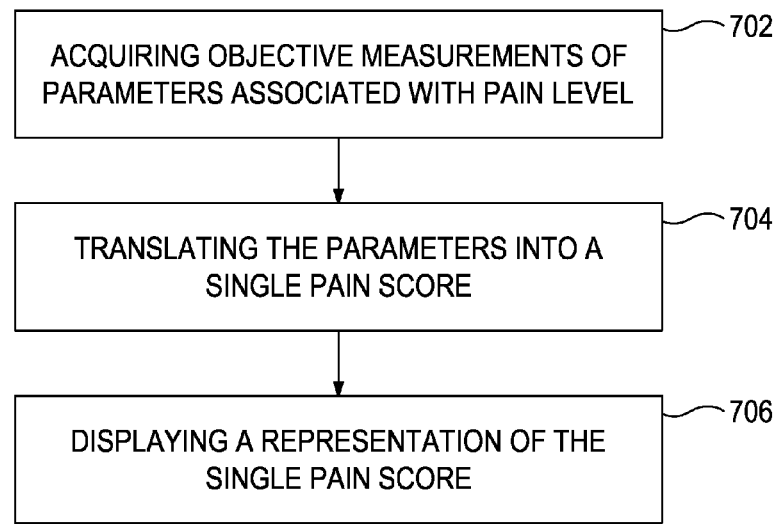
FIG. 7 illustrates a flowchart of a method for communicating pain level, in accordance with various embodiments of the subject technology.

Referring now to FIG. 7, illustrated is a flowchart of a method for communicating pain level, according to one or more embodiments of the disclosure. The method may include acquiring objective measurements of parameters associated with the pain level, as at 702. One or more of the pain level parameters may include, but are not limited to, HRM, facial EMG, and finger splaying. Other pain level parameters may be measured, depending on the application. The signal acquired to determine HRM may include a signal corresponding to heart rate (e.g., from a heart rate monitor), such as an HRV signal. The signals acquired to determine facial EMG and finger splaying may include signals corresponding to facial electromyography and hand flexing, respectively.

The method may also include translating the pain level parameters into a single pain score, as at 704. In one embodiment, the parameters are translated into the single pain score using a simple sum of the data inputs. In other embodiments, the parameters are translated into the single pain score using Boolean logic, a neural network, combinations thereof, or the like. The method may further include displaying a representation of the pain score, as at 706. In one embodiment, the pain score is displayed or otherwise represented via an ambient display, such as a frosted-glass ball or orb that changes colors or light intensity to indicate pain or its magnitude.

Thus, a process and system is disclosed that may capture, treat, store, interpret and output signals, employing interactive techniques with current technologies (e.g., tapping into the beside monitor). The combination of signals chosen, the manner of their collection (e.g., specific placement of leads) and their integration into one device may have many advantages. Applications for the subject technology may include monitoring pain and/or distress in premature infants. Other applications may include pain and distress monitoring in non-communicative populations regardless of age (e.g., critically ill individuals, the cognitively impaired, etc.) as well as potential broad applications for parental monitoring of newborn infants.

Figure 8:
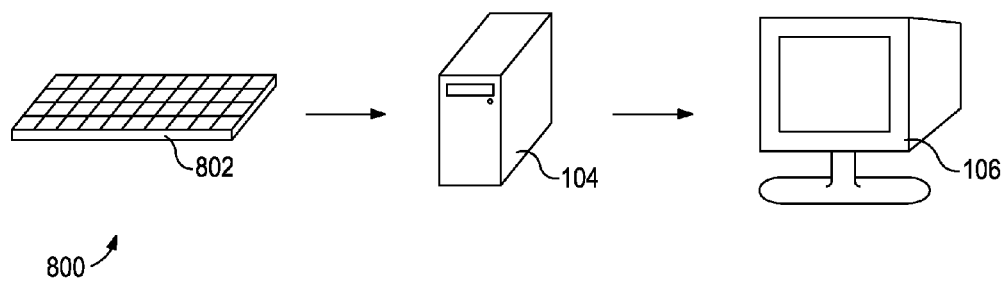
FIG. 8 illustrates an exemplary system for measuring pain or distress, in accordance with various embodiments of the subject technology.

Referring now to FIG. 8, illustrated is a system 800 for measuring pain and/or distress, in accordance with various embodiments of the subject technology. The system 800 may be substantially similar to the system 100 described above with reference to FIG. 1, excepting the differences noted and discussed below. Accordingly, the system 800 may be best understood with reference to FIG. 1 and its attendant discussion, where similar numbers correspond to similar elements that will not be described again in detail.

Similar to system 100 of FIG. 1, system 800 includes a sensory level input device 802, a processor 104, and a display 106. The system 800 may be embodied as a computer, such as a tablet PC (not illustrated), that houses the sensory level input device 802, the processor 104, and/or the display 106. Alternatively, the system 800 may be incorporated into a larger system, such as a bedside monitor or an infusion pump.

In some embodiments, the system 800 may be a standalone bedside device. For simplicity, FIG. 8 illustrates the system 800 as a standalone device with the sensory level input device 102, processor 104, and display 106. The sensory level input device 802 is configured to provide an indication of pain or distress level to the processor 104, and the processor 104 includes executable code to translate data from the sensory level input device 802 into a pain or distress score. The display 106 provides a visual representation of the pain score.

The system 800 measures, monitors, and indicates distress and/or pain associated with distressing procedures experienced by vulnerable patients (e.g., infants in the (NICU) and/or other non-communicative individuals) Each distressing procedure has an impact on the newborn causing a neural offense, and each neural offense has an associated recovery time. Infants ultimately recover after undergoing a procedure as the neural load associated with the given procedure eventually decays over time. Thus, measurement, monitoring, and/or indication of pain and distress may assist clinicians in determining, in a clinically meaningful manner, the timing, number, and impact of procedures to be performed.

The system 800 provides an objective quantification of procedural distress and provides a tool to track and display the current state of distress of a patient based on the nature of the clinical procedures undertaken. Displaying the pain or distress score in the form of a visual representation on the display 106 may inform the clinician of the current and/or predicted state of pain and distress of the patient. The availability of such a display 106 may aid clinicians in evaluating patient readiness for additional procedures. In some embodiments, the system 800 offers a live visual display of a graph (not illustrated) with an x-axis corresponding to time and a y-axis corresponding to the pain score (e.g., based on 0-10 scaling). In some embodiments, the system 800 allows "what if" evaluations and simulations of procedures in order to better plan the delivery of care so as to minimize negative health outcomes.

The sensory level input device 802 in system 800 may be a keyboard, but it may also be a touch screen device or other interface. In operation, doctors, nurses, or other clinicians may use the sensory level input device 802 by inputting an observed, estimated, or predictive pain or distress level in real-time. The distress level may be a number or other type of indication entered by the clinician based on observation or evaluation of the patient. Alternatively, or additionally, the distress level may be partially or wholly based on a distress score obtained from a "procedure load index," as will be described in more detail below.

Briefly, the procedure load index provides normalized distress scores for various pre-identified distress-causing procedures. The clinician may enter the appropriate distress level via the sensory level input device 802 by selecting one or more procedures from a list of the pre-identified distress-causing procedures. The processor 104 computes the distress score from the inputted distress level(s) and utilizes the procedure load index for the selected procedure(s) to transform the single or combined distress score into a visual representation depicted on the display 106. In some embodiments, the display 106 may be a monitor or screen (as illustrated) or any other device or apparatus capable of providing a visual representation of the distress score. In some embodiments, however, the display 106 may be a device or apparatus capable of audibly reporting the distress score, such as speakers or the like.

With both actual and theoretical distress scores, it may be useful to ascertain when the patient will be physically and/or psychologically ready to undergo additional distress-causing procedures. Accordingly, in addition to translating data acquired through the sensory level input device 802 into a distress score, the processor 104 may simultaneously calculate and project a decay rate of the distress score over time. The distress score decay rate may be applied to any particular distress score to determine when the distress score will fall below a predetermined limit. In one or more embodiments, the predetermined limit may be a fixed pain threshold number that may or may not vary between patients. In at least one embodiment, the predetermined limit is based on general conditions present during treatment, such as whether the patient is sleeping or awake, the time of day, specific feeding schedules, whether the patient is crying or calm, combinations thereof, or the like.

The decay rate projection may be simultaneously indicated in the visual representation of the distress score on the display 106, thereby allowing the clinician to determine if and when the patient is ready for additional distress-causing procedures. In one or more embodiments, the processor 104 may be configured to compound distress scores from multiple distressing procedures and provide a representation of the cumulative effects of such procedures over time. Likewise, a compounded distress score decay rate may be applied to a compounded distress score to determine the expected time at which the compound distress score will fall below the predetermined limit, and the patient will then be deemed ready to undergo additional procedures.

Figure 9:
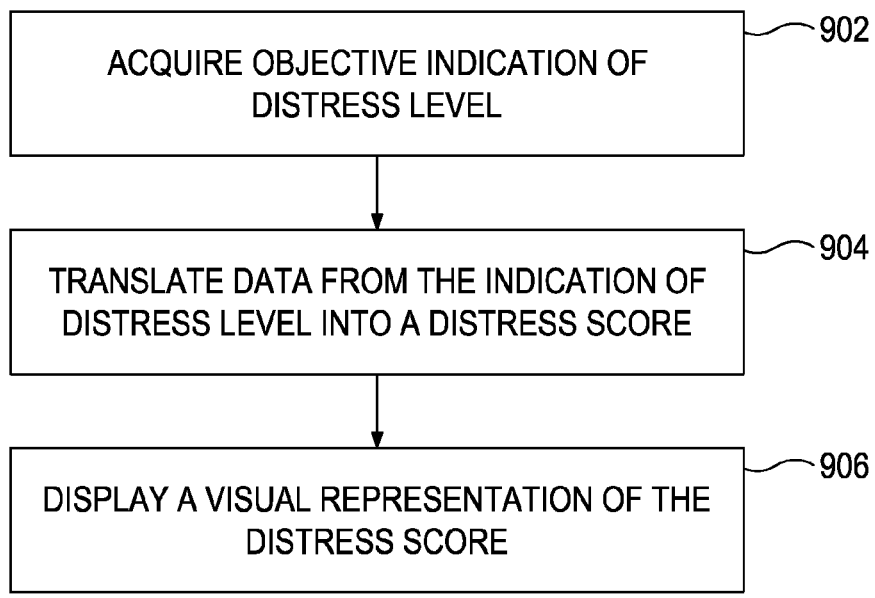
FIG. 9 illustrates a flowchart of a method for measuring pain or distress, in accordance with various embodiments of the subject technology.

Referring to FIG. 9, illustrated is a method of measuring distress, according to one or more aspects of the subject technology. The method includes acquiring an objective indication of distress level, as at 902. As briefly described above, acquiring the objective indication of distress level may involve consultation of a procedure load index, either by the clinician or by the processor 104. In the event the processor 104 consults the procedure load index, a menu may be displayed on the display 106, such that the clinician can select a particular distress-causing procedure from the menu.

The method also includes translating data acquired from the indication of distress level into a corresponding distress score, as at 904. In some embodiment, the processor 104 translates or otherwise computes the data from the distress level (or distressing procedure indication) entered by the clinician by looking up, in the procedure load index, the distress score associated with the particular distress-causing procedure. Alternatively, the clinician may manually consult the procedure load index and assign a distress score based on a particular distressing procedure. The selected distressing procedure may be one already experienced by the patient, or may be a procedure the clinician would like to simulate prior to actually undertaking the distress-causing procedure. Accordingly, future or prognosticated distress scores may be calculated and provided to the clinician for reference.

The method further includes displaying a visual representation of the calculated distress score, as at 906. In operation, the visual representation of the distress score is presented on the display 106, as generally described above. Upon viewing the displayed distress score, the clinician may be able to make an informed decision as to whether the patient is ready for the selected distressing procedures, or whether an alternative course should be pursued. It will be appreciated, however, that the representation of the calculated distress score need not be visually conveyed, but may also be conveyed audibly through, for example, audible alerts communicated through speakers or the like.

Figure 10:
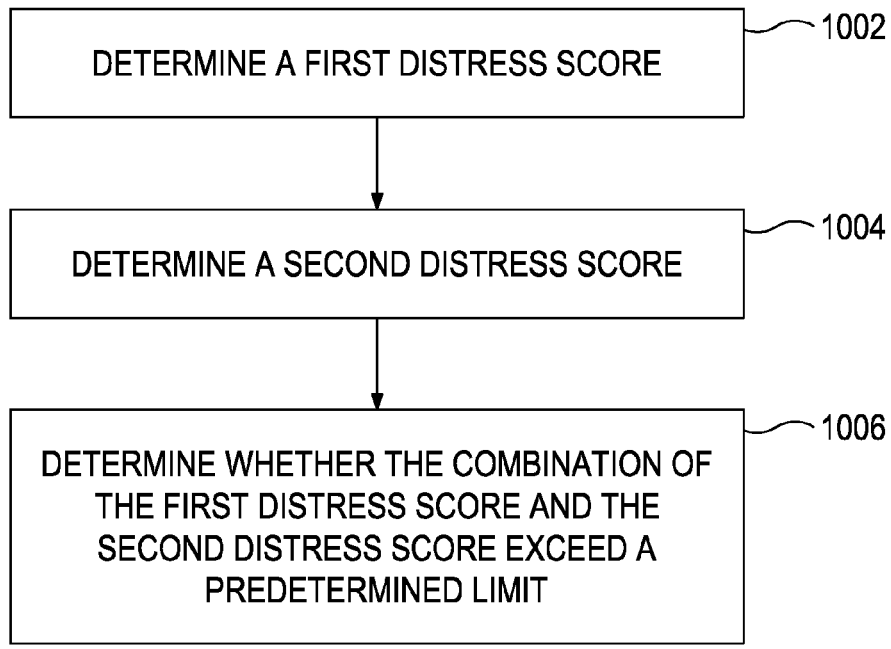
FIG. 10 illustrates a flowchart of a method for determining when to perform a distressing procedure, in accordance with various embodiments of the subject technology.

Referring now to FIG. 10, illustrated is a method for determining when to perform a distress-causing procedure, according to one or more aspects of the subject technology. The method includes determining a first distress score, as at 1002. Determining the first distress score may include acquiring an objective indication of a first distress level. In some embodiments, the objective indication of the first distress level is acquired via clinician input into the sensory level input device 802, such as through the use of the procedure load index. In some embodiments, the objective indication of the first distress level is acquired by direct measurement of distress indicators on the patient such as heart rate, temperature, respiration rate, combinations thereof, or other measurements and indications described herein. Consequently, the first distress score may be a monitored, a measured, an indicated, and/or a calculated distress score. The first distress level data may then be translated into the first distress score in the processor 104.

In any event, the first distress score may indicate lingering distress from at least one prior distressing procedure, with each procedure having a different decay magnitude and/or duration. Thus, it may be desirable for the first distress score to be calculated at a point in time of an expected additional distressing procedure, so as to determine the compound effect of the additional distressing procedure along with the past distressing procedure(s).

The method also includes determining a second distress score, as at 1004. The second distress score may be determined or otherwise calculated substantially similar to the determination of the first distress score described above, including the implementation of the procedure load index. The combination of the first and second distress scores may then be compared against a predetermined limit, as at 1006. The predetermined limit may be a fixed pain threshold number, or it may vary between patients, or be wholly or partially based on conditions present during treatment (e.g., sleeping v. awake, time of day, feeding schedules, crying v. calm, etc.). As can be appreciated, comparing the aggregate distress scores with the predetermined limit may help the clinician ascertain whether an additional distress-causing procedure is appropriate at that time, or whether additional time is recommended to allow the patient to recover.

While only two distress scores are described with reference to FIG. 10, it will be appreciated that any number of distress scores may be calculated and combined for comparison against the predetermined limit, without departing from the scope of the disclosure.

Figure 11:
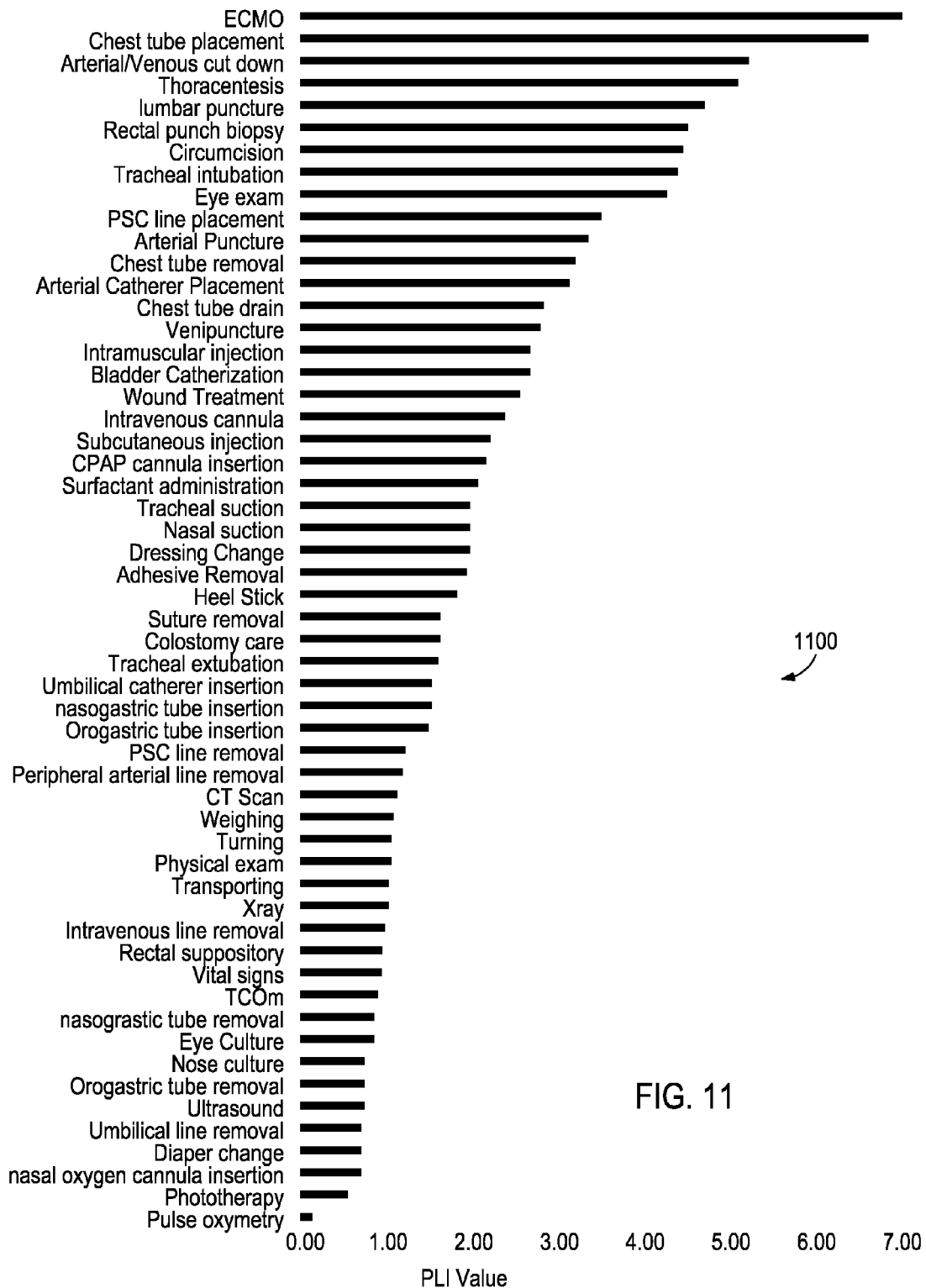
FIG. 11 illustrates a bar chart that provides procedural load index values that can be applied to various distressing procedures.

FIG. 11 illustrates a bar chart 1100 depicting exemplary procedure load index (PLI) values corresponding to several exemplary distress-causing procedures, as may be used in accordance with the subject technology. Since neonates and other non-communicative patients cannot directly state the amount of pain and/or distress experienced during potentially distressing procedures, the PLI values offer an estimated pain or distress value that can be referenced by clinicians and used by the system 800. Each PLI value indicates an initial distress score associated with the corresponding distress-causing procedure, where higher values indicate more distressful procedures.

In assigning a PLI value to a specific procedure, as discussed above, the clinician may reference the bar chart 1100, or a similarly-populated PLI chart. Over time, each initial PLI value will tend to decrease or decay, based on a number of factors, until the patient has completely, or at least substantially, recovered from the distress-causing procedure. The factors for decay may include, but are not limited to, the type of distressing procedure and the conditions of the patient, such as whether the patient is sleeping or awake.

The exemplary PLI values shown in FIG. 11 were defined or otherwise measured through a study and survey conducted of eighty-six clinicians who were asked to estimate pain or distress as it is associated with the fifty-five procedures indicated in the bar chart 1100. Two types of psychophysical techniques were used in the study to estimate the corresponding PLI values: magnitude estimation (ME) and a generalized labeled magnitude scale (gLMS).

Magnitude estimation is used to scale the intensity of the evoked perception of an applied stimulus based on Steven's power law, which states that equal stimulus ratios tend to produce equal sensation ratios. Magnitude estimation has an established history in pain or distress estimation, such as joint discomfort/mobility, pain catastrophizing, thermal pain, chronic pain, and post-operative pain. In ME, a reference stimulus or "modulus" is first given a value against which all other stimuli are subsequently compared. Thus, a respondent given the procedure "heel stick" as the modulus could rate its distress intensity at 20; if she felt that the distress magnitude of an intravenous cannula insertion, for example, were twice that of the heel stick, she would assign an intensity of 40 to that procedure. Likewise, if a diaper change were estimated to cause half the distress of a heel stick, the respondent would assign an intensity of 10 to the diaper change. Magnitude estimation has ratio level scaling properties and has been demonstrated to be a better methodology than Likert scales, particularly with variations at higher stimulus levels.

The gLMS is a semantic scale combining categorical scaling with a visual analog scale based on a quasi-logarithmic axis, and it has been demonstrated to yield psychophysical results equivalent to ME. The gLMS uses standardized wording, such as 'Low', 'Moderate', and 'Strongest Imaginable' to represent apparent sensations. While comparatively newer than ME, the gLMS is thought to be a more user friendly approach, requiring less abstraction (e.g., the consideration of stimuli as a proportion of the modulus).

Generally, in applying psychophysical techniques, respondents are asked to estimate the level or amount of a given stimulus directly experienced or imagined. In the current study, respondents were asked to estimate the magnitude (intensity of pain/distress) that various stimuli (i.e., NICU procedures) are thought or believed to produce in an infant (i.e., not themselves). This approach is referred to herein as "indirect psychophysics." Indirect, or third-party estimation of pain is common in pain research and is often referred to as "proxy rating," wherein a clinician (or a parent) estimates the pain state of a child using linear scales, such as the visual analog scale or facial pain scales. The current study used ratio-scaling psychophysical techniques, not common linear scaling, and attempted to estimate not the experience (i.e., the pain response felt or thought to be felt by self or others) but rather the amount of distress associated with a stimulus or specific procedure.

Specifically, a two-part survey was conducted to evaluate each clinician's opinion on the level of distress associated with fifty-five procedures that are commonly performed in the NICU. The subject population consisted of an estimated two hundred clinicians actively working at a level IV NICU in a research-intensive institution in the Northeastern United States. Of the estimated two hundred clinicians, eighty-six responded, the respondents being physicians and nurses providing direct care to infants in the NICU.

The survey asked respondents to estimate the distress level associated with each of the fifty-five procedures using each psychophysical technique (ME and gLMS). Thus, each procedure was rated twice by each respondent; once using each method in its given section. In ME, respondents assigned a number to a subjective sensation associated with a stimulus. Specifically, respondents were asked to enter a value for the level of distress associated with the heel stick. The heel stick is a very common procedure performed in the NICU and was assigned as the modulus or the reference stimulus against which all other stimuli were to be subsequently compared. After assigning this value, all subsequent procedures were randomly presented one at a time for comparison and rating in relationship to the modulus. For example, if a value of 10 was chosen for the heel stick and a proposed procedure was twice as distressful, 20 was entered. If it was half as distressful, 5 was entered.

Figure 12:
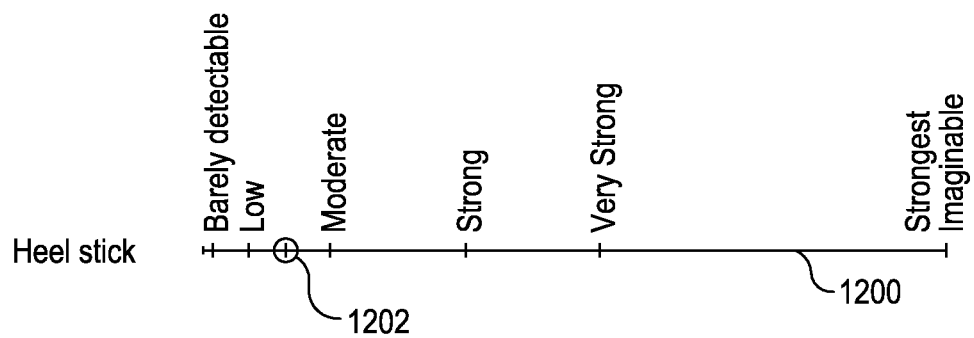
FIG. 12 illustrates an exemplary generalized labeled magnitude scale.

In gLMS, the respondents were asked to place a mark along a horizontal axis that only has verbal labels, with no numerical indicators. Referring to FIG. 12, illustrated is an example of such a horizontal axis 1200. As indicated, the horizontal axis 1200 corresponds to the heel stick procedure. The axis 1200 consists of a linear scale from 0 to 999 (numbers were invisible to respondents of the survey), and on which words were spaced in a quasi-logarithmic fashion with the labels: barely detectable, low, moderate, strong, very strong, and strongest imaginable. For each procedure, the clinicians were asked to estimate the level of distress by sliding, with a computer mouse or touchpad, an indicator 1202 along the horizontal axis 1200. Similar to ME, each procedure was individually presented, in random order, for intensity estimation.

Responses for both ME and gLMS procedures tend to have a lognormal distribution. Therefore, raw data for each set of responses for each clinician were normalized by computing the logarithm of each response value and standardized by dividing by the mean of the response values for that individual across for all procedures. An intermediate logarithmic procedure load ($PL_{log}$) for a given procedure, i, and for a given subject, k, based on either ME or gLMS responses, was computed using the following equation:

$$PL_{log}(i, k) = \frac{\log_{10}(x_{i,k} + c)}{\frac{1}{n}\sum_{j=1}^{n} \log_{10}(x_{i,j} + c)}$$

where $x_i$ is the raw response value for a given procedure, c is an additive constant, and n is the number of procedures (n=55). Values entered as zero or approximately zero, which occurred in the data, produced invalid results because $\log_{10}(0)$ is undefined. In previous analyses of this type, additive constants ranging from 0.24 to 1.0 have been used to avoid this problem. The additive constant, however, must be large enough to avoid the zero problem but small enough to avoid distortion. In this study, the constant c=0.7 satisfied both criteria and was added to each of the ME and gLMS raw values prior to analysis. The final standardized and normalized procedure load PL(i) associated with a given procedure, i, was computed by averaging the $PL_{log}(i,k)$ values across all N subjects and taking the anti-log to convert the PL back to a linear scale, according to the following equation:

$$PL(i) = 10^{[\frac{1}{N}\sum_{k=1}^{N} PL_{log}(i,k)]}$$

Both gLMS and ME responses were analyzed in the same manner. Because of the log-normal distribution trend for both ME and gLMS data, the raw data for both sets were normalized by computing the logarithms. Below are the equations used for the data analysis. Equation (1) shows how the individual responses were standardized. Equation (2) computes the procedure load associated with a given procedure as the mean of the $PL_{yi}$ across N respondents.

$$PL_{logyi} = \frac{\log_{10}(x_i + c)}{\frac{1}{n}\sum_{j=1}^{n}\log_{10}(x_j + c)} \quad (1)$$

$$PL_{logy} = \frac{1}{N}\sum_{i=1}^{N} PL_{logyi} \quad (2)$$

$$PL_y = 10^{PL_{logy}} \quad (3)$$

where N is the number of respondents, n is the number of procedures, y refers to either ME or gLMS, and c refers to the constant added. Both gLMS and ME were analyzed the same, and the final results take the anti-log of the $PL_{logy}$ values to convert back to a base 10 scale (Equation 3).

The results of the survey showed a high correlation between gLMS and ME across all procedures (r=0.95). These findings demonstrate the application of indirect psychophysical techniques in the development of a ratio-level scale to estimate procedural distress in the NICU and support the psychophysical equivalence between ME and gLMS. Consequently, a procedure load index value was computed for each of fifty-five common NICU procedures yielding two almost identical ratio level scales. These PLI values, or similarly-derived PLI values, can be referenced or otherwise used by clinicians in conjunction with the system 800 described herein in order to measure current and/or future pain or distress in vulnerable patients.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the methods disclosed is an illustration of exemplary approaches. Based upon design preferences, it is understood that the specific order or hierarchy of steps in the processes may be rearranged, or some of the steps may be performed simultaneously. The accompanying method claims present elements of the various steps in a sample order, and are not meant to be limited to the specific order or hierarchy presented.

A phrase such as an "aspect" does not imply that such aspect is essential to the subject technology or that such aspect applies to all configurations of the subject technology. A disclosure relating to an aspect may apply to all configurations, or one or more configurations. A phrase such as "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. Moreover, a phrase such as "embodiment" may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

Lastly, a reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A method of communicating a pain level of a patient, comprising:
    acquiring objective measurements of two parameters of the patient associated with the pain level and a first procedure, the parameters selected from the group consisting of heart rate variability, facial grimacing, and hand flexing;
    scaling the objective measurements, according to magnitude estimation or a generalized labeled magnitude scale, to obtain logarithmically scaled scores;
    determining, by a processor and based on the scaled scores, a pain score;
    displaying a representation of the pain score;
    calculating, by a processor, a future pain score by applying a decay rate according to a procedure load index based on data from another patient; and
    displaying a representation of the future pain score.

2. The method of claim 1, wherein acquiring the objective measurements of the two parameters associated with the pain level further comprises acquiring a signal corresponding to heart rate variability of the patient.

3. The method of claim 1, wherein acquiring the objective measurements of the two parameters associated with the pain level further comprises acquiring a signal corresponding to facial grimacing of the patient.

4. The method of claim 1, wherein acquiring the objective measurements of the two parameters associated with the pain level further comprises acquiring a signal corresponding to hand flexing of the patient.

5. The method of claim 1, wherein determining a pain score comprises one of adding the two parameters, applying Boolean logic to the two parameters, or processing the two parameters with a neural network.

6. The method of claim 1, wherein the representation of the pain score comprises a visual representation.

7. The method of claim 6, wherein the visual representation comprises visible light.

8. The method of claim 7, wherein the visible light is emitted from a ball or orb.

9. The method of claim 1, further comprising: calculating a time when a combination of the future pain score and a second pain score associated with a second procedure will fall below a predetermined limit, wherein the second pain score is determined according to the procedure load index.

10. A system for measuring and communicating pain level comprising:
- a sensory level input device configured to acquire objective measurements of two parameters selected from the group consisting of heart rate variability, facial grimacing, and hand flexing;
- a processor communicably coupled to the sensory level input device, the processor having executable code configured to (i) scale the objective measurements, according to magnitude estimation or a generalized labeled magnitude scale, to obtain logarithmically scaled scores, (ii) determine, based on the scaled scores, a pain score, and (iii) calculate a future pain score by applying a decay rate according to a procedure load index based on data from another patient; and
- a display configured to provide a representation of the pain score and a representation of the future pain score.

11. The system of claim 10, wherein the sensory level input device is configured to provide data about the parameters.

12. The system of claim 11, wherein the sensory level input device comprises two of an electrocardiogram monitor configured to provide data about heart rate variability, a facial electromyography monitor configured to provide data about facial grimacing, or a hand flexure sensor to provide data about hand flexing.

13. The system of claim 10, wherein the sensory level input device is further configured to acquire an objective measurement of, a galvanic skin response, an electroencephalography signal, or a near-infrared spectroscopy signal.

14. The system of claim 10, wherein the processor utilizes the procedure load index to determine the pain score.

15. The system of claim 10, wherein the display provides a visual representation of the pain score.

16. The system of claim 15, wherein the display comprises a ball or orb, and the visual representation comprises a colored light emitted from the ball or orb.

17. The system of claim 10, wherein the processor is further configured to calculate a time when a combination of the future pain score and a second pain score associated with a second procedure will fall below a predetermined limit, wherein the second pain score is determined according to the procedure load index.

18. A method of measuring distress in a patient, comprising:
- acquiring objective indications of two parameters associated with a distress level of the patient, the parameters being selected from the group consisting of heart rate of the patient, facial electromyography of the patient, and hand flexing of the patient;
- scaling the objective indications, according to magnitude estimation or a generalized labeled magnitude scale, to obtain logarithmically scaled scores;
- determining, based on the scaled scores, a distress score;
- displaying a representation of the distress score on a display;
- calculating, by a processor, a future distress score by applying a decay rate according to a procedure load index based on data from another patient; and
- displaying a representation of the future distress score.

19. The method of claim 18, wherein acquiring the objective indications of the distress level of the patient comprises assigning the distress level based on selection of a particular distressing procedure.

20. The method of claim 19, wherein translating data from the objective indications of the distress level into the distress score comprises looking up a pre-determined distress level associated with the particular distressing procedure in the procedure load index.

21. The method of claim 18, further comprising: calculating a time when a combination of the future distress score and a second distress score associated with a second procedure will fall below a predetermined limit, wherein the second distress score is determined according to the procedure load index.

* * * * *